July 11, 1950 H. C. SWIM Plant Pat. 963
ROSE PLANT
Filed June 29, 1949
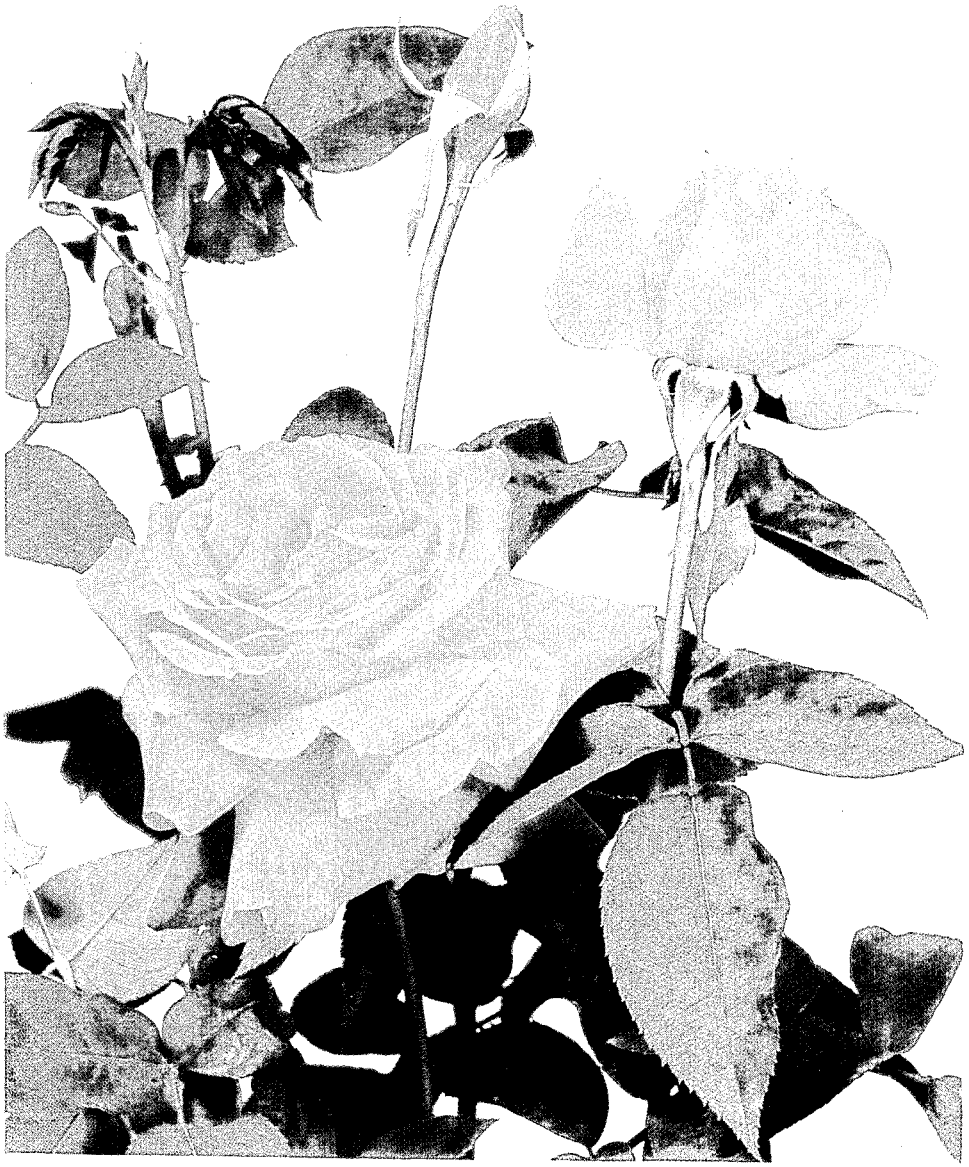
Inventor
H. C. Swim
By Robb & Robb
Attorneys Patented July 11, 1950

Plant Pat. 963

UNITED STATES PATENT OFFICE

963

ROSE PLANT

Herbert C. Swim, Ontario, Calif., assignor to Armstrong Nurseries, Inc., Ontario, Calif., a corporation of California Application June 29, 1949, Serial No. 102,100

1 Claim. (Cl. 47—61)

The present invention relates to a new and distinct variety of rose plant, originated by crossing of the varieties "Charlotte Armstrong" and the medium-sized single rose "Piccaninny" to obtain desirable characteristics of said parents and an improved hybrid tea variety easily distinguished from either of them.

This new variety is characterized as to novelty by its vigorous growing habit, with abundant, moderately large foliage, and by a flower of a distinct color and form, substantially as described and illustrated herein, with a strong damask fragrance, and produced very abundantly on normal, medium to long stems, intermittently during the growing season.

This new variety is distinguished from its seed parent in color, fragrance and abundance of foliage, more specifically described as follows:

(1) This new variety has a flower of the general color effect of Tyrian Rose, Plate 24/1 to Plate 24/2, Horticultural Colour Chart, whereas the general color effect of the flowers of "Charlotte Armstrong" is varied from Spectrum Red, Plate 1, to Rose Red, Plate 12, Ridgway's Color Standards and Nomenclature.

(2) This new variety has flowers strongly damask in fragrance, whereas the flowers of "Charlotte Armstrong" have a slight tea fragrance, and no trace of the damask fragrance.

(3) This new variety has somewhat larger and more abundant foliage than its seed parent "Charlotte Armstrong."

The new rose differs more particularly from its pollen parent also, in the following respects:

(1) The flowers of this new variety have the general color effect of Tyrian Rose, whereas those of "Piccaninny" are characterized by a very dark shade of red, popularly termed Maroon Red with a Garnet Red reverse.

(2) This new variety has semi-glossy foliage, with more than average resistance to mildew, whereas "Piccaninny" has very glossy foliage with somewhat greater susceptibility to mildew than average.

(3) This new variety is characterized by flowers having 18 to 25 petals, whereas the typical flower of "Piccaninny" contains only 5 to 6 petals.

Asexual reproduction of this new variety shows the foregoing characteristics come true to form and are established.

In the accompanying drawing specimens of the foliage and flowers at different stages of development are shown.

This new variety was asexually reproduced at Ontario, California, by budding.

The following is a detailed description of the new variety, all references to color being in accordance with the Robert F. Wilson Horticultural Colour Chart, 1938, except where indicated to be in accordance with Ridgway's Color Standards and Nomenclature:

Type: Bush; outdoor; seedling; for cut flowers and garden decoration.

Class: Hybrid tea.

Breeding: Seedling.

*Seed parent.*—"Charlotte Armstrong" (Pl. Pat. No. 455).

*Pollen parent.*—"Piccaninny" (unpatented).

Propagation: Holds its distinguishing characteristics through succeeding propagations by budding, at Ontario, California.

*Flower*

Locality where grown: Ontario, California.

Flowers borne: Sometimes singly, usually three to five to stem; in irregular cluster; on normal. medium length to long stems.

Quantity of bloom: Very abundant; outdoors.

Continuity: Intermittent during growing season.

Fragrance: Strong; damask.

Bud:

*Peduncle.*—Average length to long; average caliper; erect; moderately rough; numerous gland-tipped cilia. Color—Kildare Green, Plate XXXI (Ridgway), shaded with Oxblood Red, Plate oo823, page 191.

*Before calyx breaks.*—Size—medium. Form—Medium length, pointed; with foliaceous appendages and gland-tipped cilia on the surface of the bud; usually with slender, much cut foliaceous parts extending beyond the tip of the bud equal to one-half or more of its length.

*As calyx breaks.*—Color—Cardinal Red, Plate 822/2, page 168, with shadings of Indian Lake, Plate 826/1, page 170.

*Sepals.*—Inner surface with woolly tomentum; margins which are not covered, having gland-tipped cilia; covered margins are tomentose.

*As first petal opens.*—Size—average. Form—medium length; urn-shaped. Color—outside—Currant Red, Plate 821/3, page 167; inside—between Crimson, Plate 22, page 22, and Turkey Red, Plate 721/1, page 94; at base Sulphur Yellow, Plate 1/2, page 1.

*Opening.*—Opens up well. Is not retarded from opening by hot or dry weather.

Bloom: Size, when fully open—large; 4 inches to 5 inches.

*Petalage.*—Double; from 18 to 25 petals, plus 4 to 6 petaloids; arranged regularly.

*Form.*—High centered at first; becoming cupped; petals at first loosely rolled outward; tips becoming later at maturity loosely reflexed.

Petals:

*Texture.*—Medium thick; with inside slightly satiny and outside shiny.

*Shape.*—Outside—broadly obovate, with 1 to 2 notches. Intermediate—broadly obovate, with 1 to 2 notches. Inside—broadly obovate; scalloped, with 2 to 3 notches.

*Color.*—Colors may be modified by being shaded with other colors.

This description of a newly opened flower was made from a rose grown outdoors in the month of August, at Ontario, California:

*Color. — Outside petal* — outside surface: Phlox Pink, Plate 625/1, page 77; inside surface: Tyrian Rose, Plate 24/1, page 24.

*Intermediate petal*—outside surface: Phlox Pink, Plate 625/1, page 77; inside surface: between Tyrian Rose, Plate 24/1, page 24, and Tyrian Rose, Plate 24, page 24. *Inner petal*—outside surface: Phlox pink, Plate 625/1, page 77; inside surface: between Tyrian Rose, Plate 24/1, page 24, and Tyrian Rose, Plate 24, page 24.

This description was made from a rose that was open for three days outdoors in the month of August, at Ontario, California (Hot weather temperature 90° to 105° F.):

*Color.—Outside petal*—outside surface: Rose Bengal, Plate 25/2, page 25, with sunburnt margins of Rhodamine Purple, Plate 29/2, page 29; inside surface: Tyrian Rose, Plate 24/1, page 24, fading into Tyrian Rose, Plate 24/2, page 24, with sunburnt margins of Rhodamine Purple, Plate 29/1, page 29. *Inside petal*—outside surface: Rose Bengal, Plate 25/2, page 25; Inside surface: Tyrian Rose, Plate 24/1, page 24.

*General color effect.*—Newly opened flower—Tyrian Rose, Plate 24/1, page 24. Three days open—Tyrian Rose, Plate 24/2, page 24.

*Behavior.*—Drop off cleanly; fading in hot weather to a slightly lighter color with edges turning to Rhodamine Purple, Plate 29/1, page 29. Not affected by cold or dry weather.

*Flower longevity.*—On bush in garden—four days in August. Cut roses grown outdoors kept at living-room temperatures—three to four days in October.

*Reproductive organs*

Stamens: Many; arranged regularly about pistils, a few mixed with petaloids.

Filaments: Medium length (8 mm.); most with anthers. Color—Begonia, Plate 619/1, page 146.

Anthers: Medium size to large; all open at once approximately. Color of margins—Saffron Yellow, Plate 7/1, page 7. Central portion Saffron Yellow, Plate 7/2, page 7, with side distal to filament weakly shaded with Jasper Red, Plate o18/3, page 107.

Pollen: Abundant. Color—Buttercup Yellow, Plate 5/1, page 5.

Pistils: Average number; approximately 60 in number.

Styles: Moderately even; average length; average caliper; bunched. Color—Currant Red, Plate 821/3, page 167.

Stigma: Color — a dull-greyish translucent white.

Ovaries: All enclosed in calyx.

Hips: Average size to small; globular. Color—three-fourths mature hip, near Courge Green, Plate XVII (Ridgway). Smooth; walls medium thin.

Sepals: Permanent; long; only slightly recurved. Fresh color—inside: Parrot Green, Plate VI (Ridgway), overlaid with Oxblood Red, Plate oo823/2, page 191, with covering of white tomentum; outside: Parrot Green, Plate VI (Ridgway).

Seeds: Few in number; usually large; 2 to 4 in number.

*Plant*

Foliage:

*Leaves.*—Compound of usually five leaflets with sometimes two additional smaller leaflets; abundant; moderately large; somewhat leathery; semi-glossy.

*Leaflets.*—Shape—ovate with apex narrowly acute, base shallowly cordate to round; margin doubly serrate. Color—mature—upper surface: Dark Dull Yellow Green, Plate XXXII (Ridgway); under surface: Asphodel Green, Plate XLI (Ridgway). Young—upper surface: Burnt Lake, Plate XII (Ridgway), underlaid with Light Cress Green, Plate XXXI (Ridgway) especially along midrib; under surface: Mineral Red, Plate XXVII (Ridgway).

*Rachis.* — Average size. Upper side—grooved with many stipitate glands on edges. Under side—sparsely prickly and a few stipitate glands.

*Stipules.*—Medium length; medium width; short to medium length points turning out at an angle of more than 45°, recurved slightly toward the rachis.

*Disease.*—More than average resistant to mildew.

Growth:

*Habit.*—Bushy; upright; spreading; much branched.

*Growth.*—Very vigorous.

*Canes.*—Moderately heavy.

*Main steams.*—Color—Light Elm Green, Plate XVII (Ridgway). *Large prickles*—Several; medium length to long; almost straight, hooked slightly downward, homomorphic; with medium length narrow base. Color—between Mahogany Red, Plate II (Ridgway), and Burnt Sienna, Plate II (Ridgway). *Small prickles*—Several. Color—Mahogany Red, Plate II (Ridgway). *Hairs*—none.

*Branches.*—Color—Light Elm Green, Plate XVII (Ridgway). *Large prickles*—Several; medium length; almost straight, inclined slightly downward homomorphic declining; with moderately narrow base. Color—Reed Yellow, Plate XXX (Ridgway) overlaid with Etruscan Red, Plate XXVII (Ridgway). *Small prickles*—Several. Color—Reed Yellow, Plate XXX (Ridgway), overlaid with Etruscan Red, Plate XXVII (Ridgway). *Hairs*—none.

*New shoots.*—Color—Kildare Green, Plate XXXI (Ridgway), slightly tinged with Erythrite Red, Plate oo27, page 190. *Large Prickles*—Several; medium length; almost straight; inclined slightly downward homomorphic declining. Color—Erythrite Red, Plate oo27, page 190, tipped with Kildare Green, Plate XXXI (Ridgway). *Small prickles*—Several. Color—Erythrite Red, Plate oo27, page 190, tipped with Kildare Green, Plate XXXI (Ridgway). *Hairs*—none.

I claim:

A new and distinct variety of rose plant, characterized as to novelty by its vigorous growing habit and abundant semi-glossy foliage; by the color, petalage and form of its flower; by the strong damask fragrance of its blooms; and the abundance of the flowers produced intermittently during the growing season, substantially as shown and described.

HERBERT C. SWIM.

No references cited.